United States Patent [19]

Lange et al.

[11] Patent Number: 5,164,124

[45] Date of Patent: Nov. 17, 1992

[54] ALKALINE EARTH METAL SALTS OF VICINALLY HYDROXY, ALKOXY-SUBSTITUTED $C_{16}$–$C_{22}$ FATTY ACIDS, A PROCESS FOR THEIR PRODUCTION AND THEIR USE AS ALKOXYLATION CATALYSTS

[75] Inventors: Fritz Lange, Essen; Bert Gruber, Duesseldorf; Alfred Meffert, Monheim; Ansgar Behler, Bottrop, all of Fed. Rep. of Germany

[73] Assignee: Henkel Kommanditgesellschaft auf Aktien, Duesseldorf, Fed. Rep. of Germany

[21] Appl. No.: 160,465

[22] Filed: Feb. 24, 1988

[30] Foreign Application Priority Data

Feb. 25, 1987 [DE] Fed. Rep. of Germany ....... 3706047

[51] Int. Cl.[5] ............................... C11C 1/04
[52] U.S. Cl. ..................... 554/149; 554/156; 554/157; 554/158; 554/213; 568/618
[58] Field of Search ................. 260/413, 417

[56] References Cited

U.S. PATENT DOCUMENTS

| | | | |
|---|---|---|---|
| 2,443,280 | 6/1948 | Swern et al. | 260/413 |
| 2,485,160 | 10/1949 | Niederhauser et al. | 260/348 |
| 4,315,825 | 2/1982 | Schweizer et al. | 252/41 |
| 4,396,779 | 8/1983 | Edwards | 568/618 |
| 4,453,022 | 6/1984 | McCain et al. | 568/618 |

FOREIGN PATENT DOCUMENTS

| | | |
|---|---|---|
| 0022236 | 6/1980 | European Pat. Off. . |
| 0085167 | 12/1982 | European Pat. Off. . |
| 0127810 | 5/1984 | European Pat. Off. . |
| 0082569 | 4/1985 | European Pat. Off. . |
| 0115083 | 3/1986 | European Pat. Off. . |

OTHER PUBLICATIONS

Krane et al., Chemical Abstracts, vol. 22:5382[2], 1929.
Weygand et al., Preparative Organic Chemistry, John Wiley & Sons, N.Y., 1972, pp. 396–398.
JAOCS, vol. 63, No. 5, May 1986, Wharry et al., HAPPI, 52–54, 1986.

Primary Examiner—Jose G. Dees
Assistant Examiner—B. Frazier
Attorney, Agent, or Firm—Wayne C. Jaeschke; Henry E. Millson, Jr.; John E. Drach

[57] ABSTRACT

Alkaline earth salts of vicinally hydroxy, alkoxy-substituted $C_{16}$–$C_{22}$ fatty acids corresponding to the following general formula $$CH_3-(CH_2)_m-\underset{OR(OH)}{\overset{OH(OR)}{CH-CH}}-(CH_2)_n-COOM_{0.5}$$

in which R represents linear or branched alkyl or alkenyl groups or hydroxyalkyl groups optionally alkylated with a $C_{16}$–$C_{22}$ fatty acid, process for their preparation, and their use as catalysts. These salts give a narrow homolog distribution of the polyalkoxylation products in the catalysis of the polyalkoxylation of compounds containing active hydrogen atoms.

11 Claims, 1 Drawing Sheet

ALKALINE EARTH METAL SALTS OF VICINALLY HYDROXY, ALKOXY-SUBSTITUTED $C_{16}$-$C_{22}$ FATTY ACIDS, A PROCESS FOR THEIR PRODUCTION AND THEIR USE AS ALKOXYLATION CATALYSTS

BACKGROUND OF THE INVENTION

1. Field of the Invention

This invention relates to certain alkaline earth metal salts of vicinally hydroxy, alkoxy-substituted $C_{16}$-$C_{22}$ fatty acids, to a process for their preparation, and to their use as catalysts for the ethoxylation or propoxylation of compounds containing active hydrogen atoms.

2. Statement of Related Art:

Fatty alcohol ethoxylate and propoxylates are widely used as nonionic detergents. They are prepared by reaction of fatty alcohols normally containing from 10 to 18 carbon atoms with ethylene oxide or propylene oxide in the presence of catalysts, the fatty alcohols reacting with several molecules of ethylene oxide or propylene oxide.

The following catalysts inter alia have been used for the above-mentioned polyalkoxylation reaction:

calcium and strontium hydroxides, alkoxides and phenoxides (U.S. Pat. No. 4,453,022), calcium alkoxides (U.S. Pat. No. 4,396,779), barium hydroxide (EP-B 01 15 083), basic magnesium compounds, for example alkoxides (EP-A- 00 82 569), magnesium and calcium fatty acid salts (EP-A 0 85 167).

Other known polyalkoxylation catalysts are potassium hydroxide and sodium methylate.

The catalysts set forth above are attended inter alia by the disadvantage that they are difficult to incorporate in the reaction system and/or are difficult to produce.

A narrow range of the degree of polyalkoxylation is of particular importance to fatty alcohol polyalkoxylates, cf. JAOCS, Vol., 63, 691–695 (1986), and HAPPI, 52–54 (1986). Accordingly, so-called "narrow-range" alkoxylate have the following advantages in particular:

low pour points relatively high smoke points fewer moles of alkoxide needed to acquire solubility in water fewer hydrotropes for introduction into heavy duty liquid detergents a fainter odor attributable to the presence of free (unreacted) fatty alcohols, less pluming during spray drying.

The range of homolog distribution of fatty alcohol polyalkoxylates is essentially determined by the type of catalyst used. A measure of the homolog distribution is the so-called Q-value according to the following equation:

$$Q = n\, p^2$$

in which n is the average adduct number (mean degree of ethoxylation) and p is the percentage of adduct having a certain EO degree which is predominantly formed. Accordingly, a high Q value signifies a narrow homolog distribution range.

DESCRIPTION OF THE INVENTION

Figure 1:
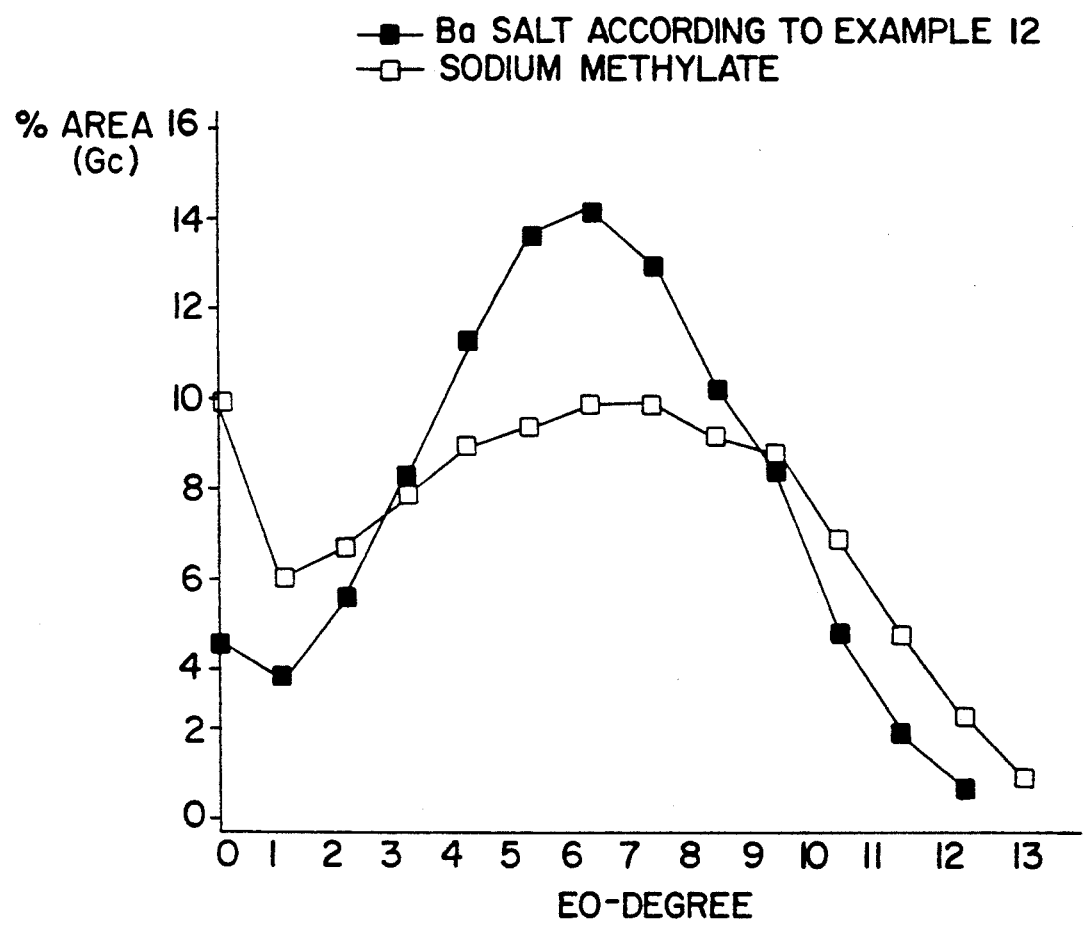
FIG. 1 is a graph showing the comparison of narrow homolog distribution of the polyethoxylation products.

Other than in the operating examples, or where otherwise indicated, all numbers expressing quantities of ingredients or reaction conditions used herein are to be understood as modified in all instances by the term "about".

This invention relates to alkaline earth metal salts of vicinally hydroxy, alkoxy-substituted $C_{16}$-$C_{22}$ fatty acids corresponding to the following general formula

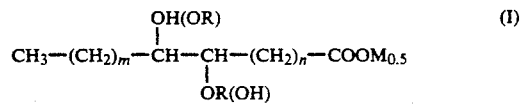

(I)

in which m and n are each integers which together make a total of 12, 14 16 or 18, M is an alkaline earth metal from the group Mg, Ca, Sr, and Ba, and R is selected from one of the following groups:

a) a linear or branched $C_1$-$C_{22}$ alkyl group b) a linear or branched, monounsaturated $C_3$-$C_{22}$ alkenyl group, c) an hydroxyalkyl group containing from 2 to 10 carbon atoms and from 1 to 5 hydroxyl groups, and d) an hydroxyalkyl group containing from 2 to 10 carbon atoms and from 1 to 5 hydroxyl groups in which a hydroxyl group is alkylated with the residue of a hydroxy-substituted $C_{16}$-$C_{22}$ carboxylic acid corresponding to the following general formula

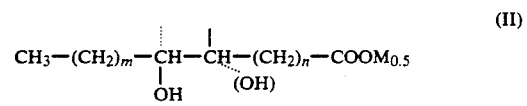

(II)

in which m, n and M are as defined above.

The present invention also relates to a process for the production of the alkaline earth salts corresponding to formula (I) and to their use as catalysts for the ethoxylation and/or propoxylation of compounds containing active H atoms, for example fatty alcohols, fatty acids and amines.

It has now been found that polyethoxylated and/or polypropoxylated fatty alcohols having a high Q value can also be obtained by using the alkaline earth salts according to the invention as ethoxylation and/or propoxylation catalysts. The alkaline earth salts according to the invention have the following advantages over the catalysts described above: (a) they permit short reaction times, (b) they are liquid or waxlike at ambient temperature and hence are easier to dose, and (c) they are soluble in the reaction system unlike, for example, alkaline earth salts according to the prior art. The same advantages are obtained where the alkaline earth salts according to the invention are used as catalysts for the ethoxylation and/or propoxylation of other compounds containing active hydrogen atoms, for example fatty acids and amines.

Although lithium soaps partly corresponding to general formula (I) (M=Li), in which the substituent R is a linear or branched, optionally unsaturated monoalcohol containing up to 18 carbon atoms, are known from U.S. Pat. No. 4,315,825, these lithium soaps are used as thickening agents for lubricating greases and are not suitable as catalysts for narrow-range polyalkoxylation.

The basic structure of the alkaline earth salts according to the invention is derived from monounsaturated fatty acids containing 16, 18, 20 or 22 carbon atoms, more especially from palmitoleic acid (9-hexadecenoic acid), petroselic acid (6-octadecenoic acid), oleic acid (9-octadecenoic acid), vaccenic acid (11-octadecenoic acid), gadoleic acid (9-eicosenoic acid), 11-eicosenoic acid, cetoleic acid (11-docosenoic acid), and eructic acid (13-docosenoic acid). These fatty acids are normally obtained from natural materials, such as tallow and/or vegetable and/or animal, including marine animal, oils, in the form of technical grade mixtures of various fatty acids with C-chain lengths in the above-stated range. Any relatively small quantities of saturated or polyunsaturated fatty acids or fatty acids containing a smaller or larger number of carbon atoms or hydroxy-substituted fatty acids, such as ricinoleic acid, which may be present in these technical grade mixtures are harmless. Pure $C_{16}$–$C_{22}$ fatty acids may of course also be used, although in most cases this is impractical for reasons of cost. The abovedescribed fatty acids can be epoxidized in the usual way in the form of their esters with $C_1$–$C_4$ alcohols, for example in accordance with U.S. Pat. No. 2,485,160 and Chemical Week, Apr. 1963, pages 55–60 and 64.

The vicinally hydroxy, alkoxy-substituted $C_{16}$–$C_{22}$ fatty acids on which the alkaline earth salts according to the invention are based are ring-opening products of the above epoxides with hydroxy compounds corresponding to the formula ROH. Due to the structure, it is not possible to indicate the carbon atom of the oxirane group at which the alkoxy radical attacks. The group R can be a linear or branched $C_1$–$C_{22}$ alkyl group, more especially a $C_1$–$C_8$ alkyl group, e.g. methyl, ethyl, propyl, butyl, pentyl, hexyl, heptyl or octyl group, and also an alkyl group derived from a $C_{10}$–$C_{22}$ fatty alcohol. R can also be an alkyl group derived from the corresponding linear or branched monounsaturated $C_3$–$C_{22}$ alkanols. Preferred are the methyl, butyl and octyl groups, and alkyl groups derived from $C_{16}$–$C_{18}$ cuts of fatty alcohols obtained from natural products.

In another embodiment of the invention, the group R can be an hydroxyalkyl group containing from 2 to 10 carbon atoms and from 1 to 5 hydroxyl groups, more especially derived from polyhydric alcohols, e.g. derived from ethylene glycol, propylene glycol, butylene glycol, glycerol, diglycerol, triglycerol, trimethylolpropane, ditrimethylolpropane, pentaerythritol, dipentaerythritol, neopentyl glycol, mannitol, and sorbitol. in ring-opening products such as these, therefore, the substituent R contains free hydroxyl groups. Provided the reaction is suitably conducted (molar ratio of epoxide to polyhydric alcohol at least 2 : 1), 1 mole of the polyhydric alcohol can react with 2 moles of the epoxidized $C_{16}$–$C_{22}$ carboxylic acid ester. After saponification and reaction to the alkaline earth salts, compounds corresponding to general formula (I) are obtained, in which R is the residue of a polyhydric alcohol which in turn is alkylated with the residue of a hydroxy-substituted $C_{16}$–$C_{22}$ carboxylic acid corresponding to general formula (II). Again, the carbon atom of the carboxylic acid at which opening of the oxirane ring takes place cannot be precisely indicated.

Preferred alkaline earth salts according to the invention are the calcium and barium salts which, in addition, can be used in the form of a mixture.

The present invention also relates to a process for the production of the alkaline earth salts according to the invention which starts out from an epoxide corresponding to the following general formula

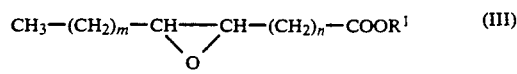

in which m and n are as defined above and $R^1$ is a $C_1$–$C_4$ alkyl group. The epoxide corresponding to general formula (III) is subjected to a ring-opening reaction with a hydroxy compound corresponding to the general formula R—OH (IV), in which R is as defined above, in the presence of acidic or alkaline catalysts. This type of reaction is known in principle, cf. Bull. Jap. Petrol. Ind. 7, 25–30 (1965), more especially pages 26 and 27. The vicinally hydroxy, alkoxy-substituted esters obtained which correspond to the following general formula

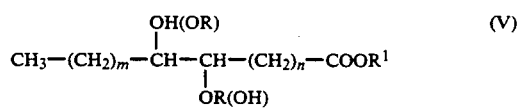

in which m, n R and $R^1$ are as defined above, is then saponified, using an alkali metal hydroxide, e.g. NaOH or KOH, and the resulting carboxylic acid alkali metal salt is acidified, and converted into an alkaline earth salt (I).

The invention is illustrated but not limited by the following examples.

Typical representatives of commercially available epoxidized oleic acid methyl esters which may be used with advantage in the process according to the invention have the chain length distribution shown in Table I.

TABLE I

Chain length distribution is % by weight of a typical oleic acid methyl ester

| | |
|---|---|
| 0–2% $C_{12}$ | |
| 2–5% $C_{14}$ | |
| 5–7% $C_{16}$ | |
| 5–7% $C_{16'}$ | (monounsaturated) |
| 1–3% $C_{18}$ | |
| 70–75% $C_{18'}$ | (monounsaturated) |
| 8–12% $C_{18''}$ | (di-unsaturated) |
| 0–1% $C_{18'''}$ | (tri-unsaturated) |
| 0–4% higher | |
| epoxide value: 4.55% by weight epoxide oxygen | |

TABLE II

Chain length distribution of the principal constituents of the oleic acid methyl ester specifically used herein (as determined by gas chromatography)

| Me Ester | % present |
|---|---|
| $C_{12}$ | 0.63 |
| $C_{14}$ | 2.74 |
| $C_{15}$ | 0.21 |
| $C_{16}$ | 4.21 |
| $C_{16'}$ | 5.01 |
| $C_{18}$ | 1.20 |
| $C_{18'}$ | 67.96 |
| $C_{18''}$ | 7.54 |
| $C_{18'''}$ | 0.72 |
| $C_{20'}$ | 1.01 |

An epoxidized oleic acid methyl ester prepared from an oleic acid methyl ester having a chain length distribution according to Table II was used in the examples.

EXAMPLES 1 to 12

A. General procedures

Alcohol and sulfuric acid were introduced into the reaction vessel and heated to the particular reaction temperature. The epoxidized fatty acid ester was then run in over a period of 1 hour and reacted over a period of another hour. The reaction mixture was then cooled to around 50° C. and neutralized with sodium methylate.

The quantities used, the reaction temperatures and the characteristic data of the hydroxy, alkoxy-stearic acid esters obtained are shown in Table III.

B. Saponification of the vicinally hydroxy, alkoxy-substituted stearic acid obtained in step A An excess of aqueous sodium hydroxide solution was added at 40° C. to the products of Examples 1 to 4 in Table III and the mixture left standing for 3 hours at 90° to 100° C. On completion of saponification, the reaction mixture was cooled to 70° C. and acidified with concentrated hydrochloric acid to a pH value of approximately 2. The aqueous phase was separated off while still hot and the product washed twice with water at 60° C. and then dried in vacuo.

The quantities used and characteristic data of the products obtained are shown in Table IV.

D. Ethoxylation with alkaline earth salts of vicinally hydroxy, alkoxy-substituted stearic acids as catalyst The catalysts was dissolved in the substance containing active hydrogen, the catalyst concentration preferably being from 0.5 to 1.5% by weight, based on the end product. The solution was transferred to an autoclave suitable for the alkoxylation reaction. The autoclave was purged with nitrogen and evacuated for 30 minutes at a temperature of 100° C. The temperature was then increased to 180° C. and the required quantity of ethylene oxide was introduced under pressure up to a pressure of 5 bar. On completion of the reaction, the mixture was left to after-react for 30 minutes.

The results obtained with the catalysts according to the invention in the ethoxylation of a commercially available lauryl alcohol (Lorol TM $C_{12}$) using the procedure described above are summarized in Table VI where:

Q = the Q-value defined above.
$n_{max}$ = degree of ethoxylation of the homolog occurring most frequently in the product in quantitative terms.
OH value, actual/desired = OH values of the polyethoxylated lauryl alcohols obtained as end product.
%-cat = catalyst concentration, based on end product.
FFA = content of free fatty alcohols in the end product in percent (GC analysis).
t = polyethoxylation reaction time.

The results of comparison tests with known catalysts

TABLE III

Ring-opening of the epoxidized oleic acid methyl ester with hydroxy compounds

| Example | Epoxy fatty acid methyl ester (g) | $H_2SO_4$ (g) | Methanol (g) | Ethylene glycol (g) | Trimethylol propane (g) | Glycerol (g) | Reaction temperature (°C.) | OH value (mg KOH/g) | Saponification value |
|---|---|---|---|---|---|---|---|---|---|
| 1 | 3868 | 8.8 | 2112 | | | | 65 | 146.5 | 170.8 |
| 2 | 3868 | 2.2 | | 2046 | | | 80 | 252.1 | 158.7 |
| 3 | 3868 | 1.65 | | | 2952 | | 90 | 343.8 | 130.4 |
| 4 | 3868 | 3.3 | | | | 2024 | 90 | 299.0 | 153.6 |

TABLE IV

Saponification of the vicinally hydroxy, alkoxy-substituted stearic acid esters according to Table III

| Example | Hydroxy, alkoxy-stearic acid ester (g) | NaOH (g) | $H_2O$ (g) | OH value (mg KOH/g) | Acid value (mg KOH/g) |
|---|---|---|---|---|---|
| 1 | 2628 | 480 | 1200 | 145.3 | 170.9 |
| 2 | 2430 | 420 | 1400 | 250.6 | 158.0 |
| 3 | 2602 | 360 | 1400 | 323.5 | 130.2 |
| 4 | 2192 | 360 | 1400 | 288.1 | 147.5 |

C. Preparation of the barium or calcium salts of the vicinally hydroxy, alkoxy-substituted stearic acids set forth in Table IV The stearic acids according to Examples 1 to 4 in Table IV were dissolved or suspended in a mixture of water and isopropanol (1 : 1) and reacted at 90° C. with equimolar quantities of barium or calcium acetate (quantity calculated from the acid value). The acetic acid released was distilled off with the solvent.

The alkaline earth salts according to Examples 1 to 4 are given in Table V below together with other prepared alkaline earth salts according to the invention.

are set out in Table VII. A commercially available lauryl alcohol was again used for polyethoxylation. The comparison shows that the compounds according to the invention give better homolog distributions (higher Q values) than potassium hydroxide, sodium methylate and calcium hydroxide. They also give equally good results compared to barium hydroxide, calcium oleate and calcium stearate but, in contrast to them, are soluble in the reaction medium. Calcium methylate, which also gives equally good results, is much more difficult to prepare and can only be handled with difficulty. Finally, the narrow homolog distribution of the polyethoxylation products obtained with the compound of Example 12 in the polyethoxylation of lauryl alcohol is shown in the form of a graph in FIG. 1 by comparison with that obtained with sodium methylate.

TABLE V

Vicinally hydroxy, alkoxy-substituted alkaline earth stearates according to the invention

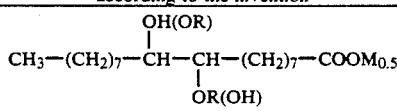

| Example | R | M |
|---|---|---|
| 1 | methyl | Ca |
| 1 | hydroxyethyl | Ca/Ba |

TABLE V-continued

Vicinally hydroxy, alkoxy-substituted alkaline earth stearates according to the invention

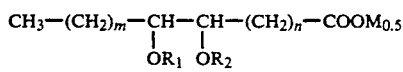

$$CH_3-(CH_2)_7-\underset{\underset{OR(OH)}{|}}{CH}-\underset{\underset{}{|}}{CH}-(CH_2)_7-COOM_{0.5}$$

| Example | R | M |
|---|---|---|
| 3 | trimethylolpropyl | Ca |
| 4 | 2,3-dihydroxypropyl | Ca |
| 5 | $C_8$ alkyl | Ca |
| 6 | $C_8$ alkyl | Ba |
| 7 | $C_{16}$–$C_{18}'$ alkyl | Ca |
| 8 | $C_{16}$–$C_{18}'$ alkyl | Ba |
| 9 | 4-hydroxybutyl | Ca |
| 10 | 4-hydroxybutyl | Ba |
| 11 | trimethylolpropyl | Ba |
| 12 | 2,3-dihydroxypropyl | Ba |

TABLE VI

Ethoxylation of a commercially available lauryl alcohol (Lorol ™ $C_{12}$) using the compounds of the invention as catalyst

| Cat. of Example no. | % cat. | Reaction time (h) | Q | $n_{max.}$ | OH value actual | OH value desired | FFA (%) |
|---|---|---|---|---|---|---|---|
| 1 | 1 | 7 | 1244 | 6 | 129.8 | 125.7 | 6.2 |
| 2 | 0.5 | 10.5 | 1161 | 6 | 137.9 | 130.0 | 4.2 |
| 3 | 0.5 | 7 | 1144 | 6 | 126.5 | 125.2 | 4.5 |
| 4 | 5 | 6 | 985 | 6 | 134.4 | 134.1 | 6.9 |
| 5 | 0.5 | 1.5 | 1242 | 6 | 125.5 | 123.7 | 4.2 |
| 6 | 0.1 | 8.5 | 1297 | 6 | 126.9 | 125.7 | 8.5 |
| 7 | 5 | 4 | 1217 | 5 | 127.9 | 119.8 | 7 |
| 8 | 0.5 | 4 | 1123 | 6 | 130.0 | 124.7 | 6 |
| 9 | 0.5 | 14.5 | 1210 | 6 | 125.4 | 125.7 | 3.3 |
| 10 | 0.5 | 4 | 1061 | 5 | 127.9 | 123.7 | 5.2 |
| 11 | 0.5 | 3 | 1081 | 5 | 146 | 131.2 | 6 |
| 12 | 0.5 | 1.5 | 1286 | 6 | 128.3 | 128.4 | 4.2 |

TABLE VII

Ethoxylation of a commercially available lauryl alcohol (Lorol ™ $C_{12}$) using known catalysts

| Catalyst | % cat. | Reaction time (h) | Q | $n_{max.}$ | OH value actual | OH value desired | FFA (%) |
|---|---|---|---|---|---|---|---|
| KOH | 0.5 | 3.5 | 611 | 6 | 125.1 | 125.2 | 7.5 |
| $NaOCH_3$ | 0.5 | 4.0 | 595 | 6 | 128.8 | 126.8 | 9.9 |
| $Ca(OH)_2$ | 0.5 | 11.0 | 695 | 6 | 136.8 | 126.3 | 9.4 |
| $Ba(OH)_2$ | 1.0 | 4.0 | 1225 | 6 | 129.3 | 128.4 | 3.8 |
| Ca oleate | 0.5 | 10.5 | 1272 | 6 | 126.7 | 128.4 | 5.1 |
| Ca stearate | 1.0 | 7.5 | 1251 | 6 | 132.8 | 129.5 | 5.0 |
| Ca ethylate | 0.5 | 8.0 | 1316 | 6 | 130.2 | 125.7 | 4.5 |

We claim:

1. An alkaline earth metal salt of a vicinal hydroxy-, alkoxy-substituted $C_{16}$–$C_{22}$ fatty acid of the formula $$CH_3-(CH_2)_m-\underset{\underset{OR_1}{|}}{CH}-\underset{\underset{OR_2}{|}}{CH}-(CH_2)_n-COOM_{0.5}$$

wherein m and n are integers which when taken together equal 12, 14, 16, or 18; M is an alkaline earth metal selected from the group consisting of Mg, Ca, Sr, and Ba; $R_1$ and $R_2$ are separately (1) hydrogen, or (2) an aliphatic radical selected from the group consisting of: (a) a straight- or branched-chain $C_1$–$C_{22}$ alkyl group; (b) a straight- or branched-chain monounsaturated $C_3$–$C_{22}$ alkenyl group; (c) a hydroxyalkyl group having from 2 to 10 carbon atoms and from 1 to 5 hydroxyl groups; (d) a hydroxyalkyl group having from 2 to 10 carbon atoms and from 1 to 5 hydroxyl groups in which a hydroxyl group is alkylated with the residue of a hydroxy-substituted $C_{16}$–$C_{22}$ carboxylic acid of the formula II

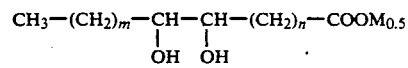

$$CH_3-(CH_2)_m-\underset{\underset{OH}{|}}{CH}-\underset{\underset{OH}{|}}{CH}-(CH_2)_n-COOM_{0.5} \quad \text{II}$$

wherein m and n are defined as above, with the proviso that when $R_1$ is hydrogen, $R_2$ is defined as in (2) above and when $R_2$ is hydrogen $R_1$ is defined as in (2) above.

2. The alkaline earth metal salt of claim 1 wherein $R_1$ and $R_2$ are separately (1) hydrogen or (2) a $C_1$–$C_8$ alkyl group with the proviso that when $R_1$ is hydrogen, $R_2$ is a $C_1$–$C_8$ alkyl group and when $R_2$ is hydrogen, $R_1$ is a $C_1$–$C_8$ alkyl group.

3. The alkaline earth metal salt of claim 1 wherein $R_1$ and $R_2$ are separately (1) hydrogen or (2) a methyl, butyl, or octyl group with the proviso that when $R_1$ is hydrogen, $R_2$ is a methyl, butyl, or octyl group and when $R_2$ is hydrogen, $R_1$ is a methyl, butyl, or octyl group.

4. The alkaline earth metal salt of claim 1 wherein $R_1$ and $R_2$ are separately (1) hydrogen or (2) an alkyl or alkenyl group derived from a natural $C_{16}$–$C_{18}$ fatty alcohol with the proviso that when $R_1$ is hydrogen, $R_2$ is an alkyl or alkenyl group derived from a natural $C_{16}$–$C_{18}$ fatty alcohol and when $R_2$ is hydrogen, $R_1$ is an alkyl or alkenyl group derived from a natural $C_{16}$–$C_{18}$ fatty alcohol.

5. The alkaline earth metal salt of claim 1 wherein $R_1$ and $R_2$ are separately (1) hydrogen or (2) a hydroxyalkyl group is a derived from a hydroxyalkyl compound selected from the group consisting of ethylene glycol, propylene glycol, butylene glycol, glycerol, diglycerol, triglycerol, trimethylolpropane, di-trimethylolpropane, pentaerythritol, dipentaerythritol, neopentyl glycol, mannitol, or sorbitol with the proviso that when $R_1$ is hydrogen, $R_2$ is a hydroxyalkyl group is a derived from a hydroxyalkyl radical selected from the group consisting of ethylene glycol, propylene glycol, butylene glycol, glycerol, diglycerol, triglycerol, trimethylolpropane, di-trimethylolpropane, pentaerythritol, dipentaerythritol, neopentyl glycol, mannitol, or sorbitol and when $R_2$ is hydrogen, $R_1$ is a hydroxyalkyl group is a derived from a hydroxyalkyl radical selected from the group consisting of ethylene glycol, propylene glycol, butylene glycol, glycerol, diglycerol, triglycerol, trimethylolpropane, di-trimethylolpropane, pentaerythritol, dipentaerythritol, neopentyl glycol, mannitol, or sorbitol.

6. The alkaline earth metal salt of claim 1 wherein M is Ca or Ba.

7. In a method for making a polyalkoxylated compound which comprises reacting a compound having an active hydrogen atom selected from the group consisting of a fatty alcohol, fatty acid, or fatty amine with ethylene oxide and/or propylene oxide in the presence of a catalyst-effective amount of an alkoxylation catalyst the improvement comprising reacting said active hydrogen compound with ethylene oxide and/or propylene oxide in the presence of a catalyst-effective amount of a alkaline earth metal salt of claim 1.

8. The method of claim 7 wherein said improvement comprises reacting said active hydrogen compound with ethylene oxide and/or propylene oxide in the presence of a catalyst-effective amount of a alkaline earth metal salt of claim 15.

9. The method of claim 7 wherein said improvement comprises reacting said active hydrogen compound with ethylene oxide and/or propylene oxide in the presence of a catalyst-effective amount of a alkaline earth metal salt of claim 17.

10. The method of claim 7 wherein said improvement comprises reacting said active hydrogen compound with ethylene oxide and/or propylene oxide in the presence of a catalyst-effective amount of a alkaline earth metal salt of claim 18.

11. The method of claim 7 wherein said improvement comprises reacting said active hydrogen compound with ethylene oxide and/or propylene oxide in the presence of a catalyst-effective amount of a alkaline earth metal salt of claim 19.

* * * * *

UNITED STATES PATENT AND TRADEMARK OFFICE
CERTIFICATE OF CORRECTION

PATENT NO. : 5,164,124
DATED : Nov. 17, 1992
INVENTOR(S) : Lange et al.

It is certified that error appears in the above-identified patent and that said Letters Patent is hereby corrected as shown below:

In claim 8, column 9, line 3, "claim 15" should read -- claim 2 --.

In claim 9, column 9, line 8, "claim 17" should read -- claim 4 --.

In claim 10, column 10, line 3, "claim 18" should read -- claim 5 --.

In claim 11, column 10, line 9, "claim 19" should read -- claim 6 --.

Signed and Sealed this

Nineteenth Day of April, 1994

Attest:

BRUCE LEHMAN

*Attesting Officer*      *Commissioner of Patents and Trademarks*